United States Patent
Arai et al.

(10) Patent No.: US 6,776,860 B2
(45) Date of Patent: Aug. 17, 2004

(54) CERAMIC COMPOSITE AND MANUFACTURING METHOD THEREOF

(75) Inventors: Kaoru Arai, Saitama (JP); Masahiro Kohketsu, Saitama (JP); Asako Matsushima, Saitama (JP); Masanori Nakasu, Tokyo (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 09/450,511

(22) Filed: Nov. 30, 1999

(65) Prior Publication Data

US 2002/0104602 A1 Aug. 8, 2002

(30) Foreign Application Priority Data

Nov. 30, 1998 (JP) .......................................... 10-340459

(51) Int. Cl.$^7$ .......................... B32B 31/06; B32B 31/26; A61F 2/28
(52) U.S. Cl. ................. 156/89.11; 428/701; 623/23.56; 623/901
(58) Field of Search ................................ 428/699, 701, 428/702; 156/89.11, 89.23; 623/23.56, 901

(56) References Cited

U.S. PATENT DOCUMENTS

| | | | |
|---|---|---|---|
| 4,218,255 A | | 8/1980 | Bajpai et al. |
| 4,293,540 A | | 10/1981 | Shikita et al. |
| 4,419,161 A | * | 12/1983 | Hailey |
| 4,529,459 A | * | 7/1985 | Ebata et al. |
| 4,767,479 A | * | 8/1988 | Ferguson et al. |
| 4,878,914 A | | 11/1989 | Miwa et al. |
| 5,030,396 A | * | 7/1991 | Saita et al. |
| 5,030,611 A | * | 7/1991 | Ogawa et al. |
| 5,055,307 A | | 10/1991 | Tsuru et al. |
| 5,128,169 A | * | 7/1992 | Saita et al. |
| 5,137,534 A | * | 8/1992 | Sumita |
| 5,141,510 A | * | 8/1992 | Takagi et al. |
| 5,152,791 A | * | 10/1992 | Hakamatsuka et al. |
| 5,645,596 A | * | 7/1997 | Kim et al. |
| 5,702,677 A | * | 12/1997 | Shimp et al. |
| 5,783,248 A | | 7/1998 | Lin et al. |
| 5,851,670 A | | 12/1998 | Mitoh et al. |
| 5,897,953 A | | 4/1999 | Ogawa et al. |
| 5,919,473 A | | 7/1999 | Elkhoury |
| 5,954,900 A | * | 9/1999 | Hegner et al. |
| 5,980,572 A | * | 11/1999 | Kim et al. |
| 6,040,196 A | | 3/2000 | Mitoh et al. |
| 6,149,688 A | * | 11/2000 | Brosnahan et al. |
| 6,159,437 A | * | 12/2000 | Itoi et al. |

FOREIGN PATENT DOCUMENTS

| | | | |
|---|---|---|---|
| JP | 2-225382 | * | 9/1990 |
| JP | 9-142817 | * | 6/1997 |
| JP | 10279471 | | 10/1998 |
| WO | 98/17330 | | 4/1998 |
| WO | 98/38948 | | 9/1998 |

OTHER PUBLICATIONS

David W. Richerson, "Modern Ceramic Engineering," Marcel Dekker, Inc. 2$^{nd}$ Edition, 1992, pp. 519–522.*

M. Otsuka et al., "Controlled Drug Release from Hetero Porous Hydroxyapatite Block"(with English translation).

* cited by examiner

Primary Examiner—Melvin C. Mayes
(74) Attorney, Agent, or Firm—Greenblum & Bernstein, P.L.C.

(57) ABSTRACT

A method of manufacturing a ceramic composite comprises the steps of preparing at least two ceramics bodies to be bonded together, each of the at least two ceramics bodies having a bonding surface; preparing a slurry in which primary particles of a bonding ceramic are dispersed; applying the slurry to the bonding surface of at least one of the ceramic bodies to be bonded; and sintering the ceramic bodies between which the slurry has been interposed to bond them. In this method, the bonding ceramic in the slurry is preferably constituted from the same ceramic starting material as that of the at least one of the ceramic bodies to be bonded. In this way, it becomes possible to manufacture, with a simple technique, a ceramic composite having a required strength and excellent biocompatibility and biosafety.

15 Claims, 6 Drawing Sheets

FRONT ←——————→ BACK

CERAMIC COMPOSITE AND MANUFACTURING METHOD THEREOF

BACKGROUND OF THE INVENTION

1. Field of the Invention

The present invention relates to a ceramic composite and a manufacturing method thereof, and more particularly to a method for manufacturing a ceramic composite suitable for medical applications, and to a ceramic composite manufactured by this method.

2. Description of the Related Art

Hydroxyapatite, which is a calcium phosphate-based ceramic, has the same structure as inorganic bone components. For this reason, hydroxyapatite has excellent biocompatibility and thus is used for various biocompatible materials such as artificial dental implants, bone replacement materials, dental cements, and the like.

In clinical practice, hydroxyapatite is used by being formed into dense articles, granular articles, porous articles having arbitrary porosity, or the like.

Dense hydroxyapatite articles have sufficient strength required for implant materials. However, because of its dense structure, these articles involve problems in that they impede circulation of body fluids such as blood and they have a poor bonding ability to the surrounding bone tissue when implanted in the living body.

In contrast with this, porous hydroxyapatite articles allow blood and other fluids to pass through the pores. Such porous hydroxyapatite articles are advantageous in that they are quickly surrounded by newly formed bone cells, and thus have a good bonding ability to bone tissue. On the other hand, however, such porous hydroxyapatite articles involve a problem in that it is difficult to maintain sufficient strength required for implant materials.

In view of the above-described problems, attempts have been made to provide a hydroxyapatite ceramic composite composed of hydroxyapatite ceramic bodies having different porosities.

As a method for producing such a ceramic composite, it has been proposed to produce a dense ceramic body and a porous ceramic body, and then to bond these bodies using a shrinkage fitting method in which the bodies are fitted together by utilizing a difference in the coefficients of thermal shrinkage therebetween. This method was disclosed by Japanese Patent No. 1677470.

However, when the ceramic bodies to be bonded together possess similar coefficients of thermal shrinkage, it is difficult to bond these bodies with the above-mentioned method. Further, in the case where the ceramic bodies are bonded together with this method, the shapes of the fitted sections of respective ceramic bodies have to be in advance determined taking heat-induced dimensional changes and the like which will occur into consideration. However, it is difficult to pre-adjust the densities, dimensions, and other characteristics of ceramic bodies to be bonded together by taking the heat-induced dimensional changes into consideration. Furthermore, the ceramic bodies to be bonded have limitations in their shapes, since these ceramic bodies have to be formed into fittable shapes.

Another method has also been proposed to bond ceramic bodies together, in which the ceramic bodies are bonded together by interposing an intermediate layer such as a resin-containing adhesive and the like therebetween.

This method imposes no limitations on the materials, shapes, or other characteristics of the ceramic bodies to be bonded, because there is no need to take heat-induced dimensional changes or the like into consideration. However, when an adhesive or the like is used to bond ceramic bodies together, it is difficult to obtain a ceramic composite having adequate bonding strength. Further, even if such a ceramic composite could be obtained, it is difficult to maintain the bonding strength for a long time. Furthermore, when ceramic composites containing adhesives or the like are applied to the living body, there is a danger that the resins and other components contained in the adhesive will elute into the living body.

Therefore, the method using the adhesive described above involves problems in terms of biosafety and bioaffinity.

SUMMARY OF THE INVENTION

It is therefore an object of the present invention to provide a method of manufacturing ceramic composite that can manufacture, with a simple technique, a ceramic composite having required strength and excellent bioaffinity and biosafety.

Further, another object of the present invention is to provide a ceramic composite which has required strength and excellent bioaffinity and biosafety and which can be obtained with a simple manufacturing method.

In view of these objects, the present invention is directed to a method of manufacturing a ceramic composite. The method comprising the steps of: preparing at least two ceramics bodies to be bonded together, each of the at least two ceramics bodies having a bonding surface; preparing a slurry in which primary particles of a bonding ceramic are dispersed; applying the slurry to the bonding surface of at least one of the ceramic bodies to be bonded; and sintering the ceramic bodies between which the slurry has been interposed to bond them.

According to the method of manufacturing the ceramic composite of the present invention, it is possible to bond a plurality of ceramic bodies with a simple technique. Further, the slurry in which primary particles of a bonding ceramic are dispersed is applied to the bonding surface of one of the ceramic bodies to be bonded, it becomes possible to obtain the ceramic composite having an excellent bonding strength by sintering such ceramic bodies. Further, it becomes possible to completely integrate the ceramic bodies with each other, thereby preventing the strength at the bonding area between the sintered ceramic bodies from being deteriorated. Further, according to the present invention, it is possible to easily manufacture ceramic composites having complex shapes.

In the present invention, it is preferred that the at least two ceramics bodies have different porosities. Bonding the ceramic bodies having such different porosities together makes it possible to obtain a ceramic composite in which different sections exhibit different functions. Therefore, it becomes possible to manufacture, with a simple technique, a ceramic composite (e.g., biocompatible materials such as artificial dental implants, bone replacement materials, dental cements and the like) having the required strength and excellent bioaffinity and biosafety. In this case, it is preferable that the at least one of the ceramic bodies has a porosity of 15 to 70%.

Further, in the present invention, it is also preferred that the at least two ceramics bodies have the identical compositions. Preferably, the at least one of the ceramic bodies is composed of calcium phosphate-based compounds. More preferably, the at least one of the ceramic bodies is composed of calcium phosphate-based compounds with a Ca/P ratio of 1.0 to 2.0. In this case, it is preferable that the calcium phosphate-based compounds is hydroxyapatite.

Further, in the present invention, it is also preferred that the bonding ceramic in the slurry is constituted from the same material as that of at least one of the ceramic bodies to be bonded, and that the slurry does not contain any resin components therein. This means that the slurry that is applied to the ceramic bodies to be bonded does not contain any water-soluble polymers such as binders, that is the ceramic composite does not contain any organic components. Accordingly, the ceramic composite of the present invention eliminates the danger that these organic components will elute into the living body when this ceramic composite is used as a biocompatible material. In this case, it is preferred that the content of the bonding ceramic in the slurry is 0.1 to 20 vol %.

Furthermore, in the present invention, it is also preferred that the particles of the bonding ceramic have an average grain size of 0.05 to 0.5 µm. Further, it is preferred that the bonding ceramic is composed of calcium phosphate-based compounds, and that the particles of the bonding ceramic have an average grain size of 0.05 to 0.5 µm.

Moreover, it is also preferred that the bonding ceramic is composed of calcium phosphate-based compounds. Preferably, the bonding ceramic is composed of calcium phosphate-based compounds with a Ca/P ratio of 1.0 to 2.0. Further, more preferably, the calcium phosphate-based compounds is hydroxyapatite.

In the present invention, it is preferred that the step of sintering the ceramic bodies is carried out in accordance with a non-pressure sintering method. Further, it is also preferred that the step of sintering the ceramic bodies is carried out at a temperature from 900 to 1300° C.

The present invention is also directed to a ceramic composite manufactured in accordance with the method as described above. The ceramic composite preferably includes a bone replacement material.

These and other objects, structures and advantages of the present invention will be apparent more clearly from the following description of the invention based on the examples.

DETAILED DESCRIPTION OF THE PREFERRED EMBODIMENTS

Figure 1:
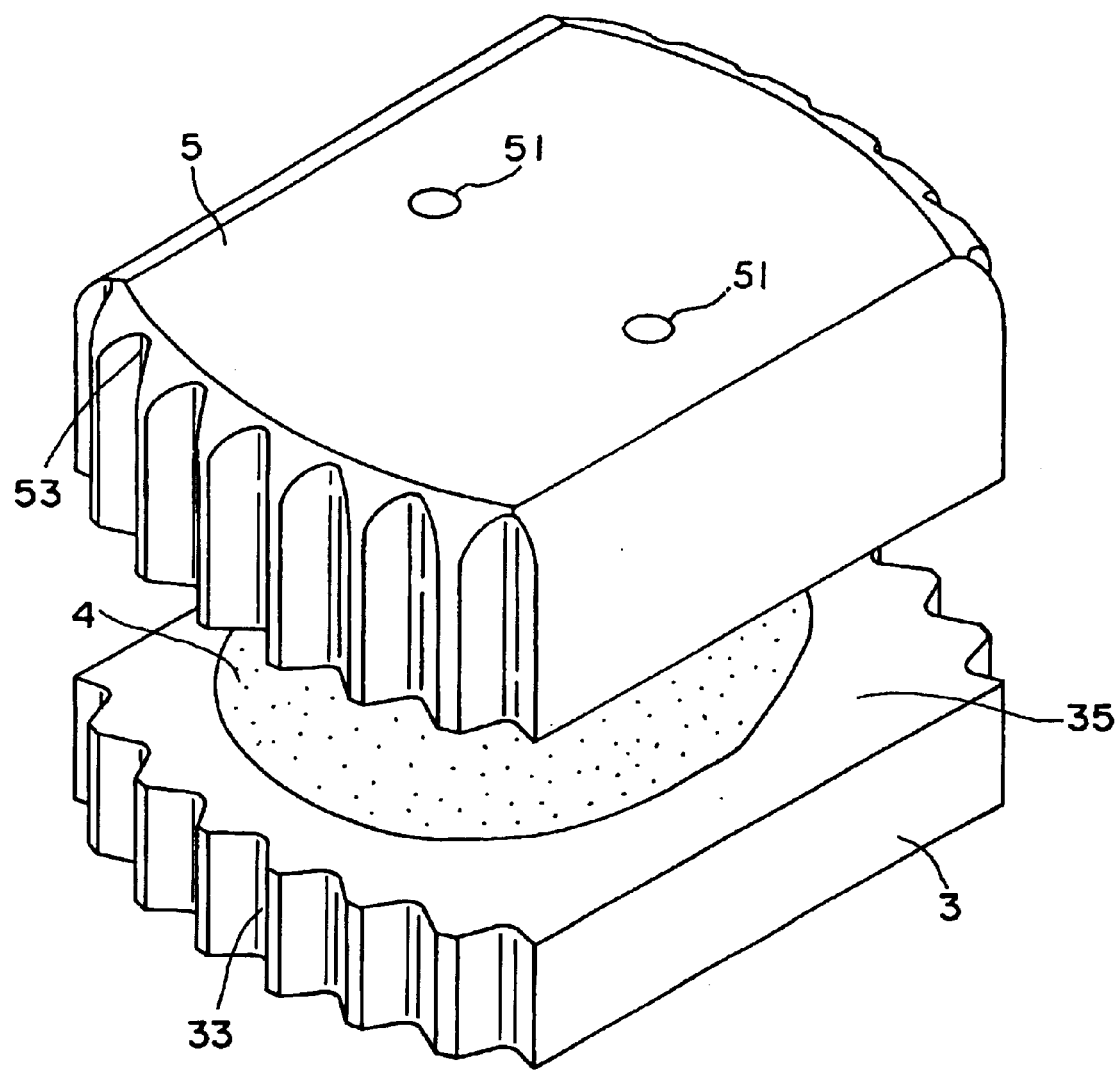
FIG. 1 is a perspective view of ceramic bodies to be bonded in accordance with a method of the present invention, which shows a state that slurry is applied to a bonding surface of one of ceramic bodies.

Hereinafter, a detail description of a method of manufacturing a ceramic composite according to the present invention and a ceramic composite manufactured by the method will be given.

Namely, the present invention is directed to a method of manufacturing a ceramic composite suitable for medical applications, and also directed to a ceramic composite manufactured by the method. The feature of the present invention is to interpose a slurry, in which primary particles of a bonding ceramic are dispersed, between the bonding surfaces of ceramic bodies to be bonded together and then sinter them to obtain a ceramic composite.

This feature makes it possible to firmly bond the ceramic bodies together to obtain a continuously integrated ceramic composite having no boundary surface.

In this regard, the properties of the ceramic bodies to be bonded are not limited in any particular way. Specifically, the ceramic bodies to be bonded may have identical or different properties. However, in a preferred practice, ceramic bodies having different porosities are bonded to each other.

Bonding ceramic bodies having different porosities together makes it possible to obtain a ceramic composite in which different sections exhibit different required functions despite the fact that the bonded composite is a monolithic structure.

When this ceramic composite is used as, for example, a bone replacement material (e.g., vertebral body spacer) to be implanted into a cervical vertebra, spinal column or the like, the ceramic composite can be formed such that different sections have different porosities. For example, it is possible to form a ceramic composite which includes low-porosity portions having excellent strength and high-porosity portions having excellent fluid circulation capabilities.

In this case, it is preferred that the high porosity portions are arranged in sections of the ceramic composite which will be in contact with bones or tissues when implanted, which makes it possible to promote cohesion with bones and tissues. On the other hand, it is preferred that the low porosity portions are arranged in sections of the ceramic composite which serve to maintain the shape of the implanted space for the ceramic composite or serve to support the bones adjacent to the implanted space.

Further, in this case, various manufacturing methods can be used for manufacturing the ceramic bodies to be bonded together.

For example, a dense ceramic body may be manufactured in the following manner. Specifically, a starting material ceramic powder is first prepared in accordance with a wet or dry process. Subsequently, the starting material ceramic powder is pressurized by means of a mold press, rubber press or the like to form a compacted body having a predetermined shape. Thus formed compacted body is then sintered at a specific temperature to obtain a dense ceramic body.

Further, a porous ceramic body may be manufactured in the following manner, for example. Specifically, a starting material ceramic powder is first prepared in accordance with a wet or dry process. Subsequently, water, a foaming agent and the like are added to the prepared starting material ceramic powder, and then the mixed solution containing them is agitated. Next, the agitated mixture is dried at about 80° C., for example, to form a dried body having a predetermined shape. A porous ceramic body is obtained by sintering the dried body at a specific temperature. In this connection, examples of foaming agents include organic substance having thermal decomposition property, such as hydrogen peroxide, methylcellulose and the like, and other substances.

The porosity of the porous ceramic body may be adjusted by varying the amount of the foaming agent to be added; the viscosity (that is, the ratio of powder and liquid) of the mixture containing the foaming agent and the starting material ceramic powder; the agitating conditions of the mixed solution; or the like.

The porosity of the porous ceramic body is not limited in any particular value, and it can be appropriately set in accordance with the intended application of the ceramic composite.

When the ceramic composite is to be used as a biocompatible material, at least one of the ceramic bodies to be bonded should have a porosity of 15 to 70%, and preferably 30 to 55%.

In addition, ceramic bodies to be bonded may have different compositions, but it is preferred that they have the identical compositions. In this connection, it is to be noted that bonding defects may occur during sintering process if ceramic bodies to be bonded have different compositions and they possess significantly different coefficients of thermal shrinkage.

No limitations are imposed on the materials that constitute the ceramic bodies. Preferably, ceramic materials that have bioaffinity and biosafety should be used as constituent materials for the ceramic bodies. In other words, various ceramic materials having biocompatibility can be used.

Examples of ceramic materials that can be used as such biocompatible materials include alumina, zirconia, calcium phosphate-based compounds, and the like. In this connection, calcium phosphate-based compounds are preferably used as the biocompatible materials, since calcium phosphate-based compounds can remain stable in the living body for a long time and therefore they are particularly suitable for biocompatible materials.

Examples of calcium phosphate-based compounds include hydroxyapatite ($Ca_{10}(PO_4)_6(OH)_2$), TCP($Ca_3(PO_4)_2$), $Ca_2P_2O_7$, $Ca(PO_3)_2$, $Ca_{10}(PO_4)_6F_2$, $Ca_{10}(PO_4)_6C_{12}$, DCPD($CaHPO_4 \cdot 2H_2O$), and $Ca_4O(PO_4)_2$. These may be used individually or as mixtures of two or more compounds.

The Ca/P ratio of such a calcium phosphate-based compound should preferably be 1.0 to 2.0. A calcium phosphate-based compound whose Ca/P ratio lies within this range has excellent biostability and biocompatibility, and is thus suitable for a biocompatible material. When a ceramic body is a mixture containing various kinds of calcium phosphate-based compounds, the Ca/P ratio of the mixture should preferably lie within the above-mentioned range.

Among the calcium phosphate-based compounds, hydroxyapatite is extremely suitable for biocompatible materials such as artificial bone, artificial dental implants and the like, since hydroxyapatite has a structure that is similar to bone or dental tissue. Therefore, hydroxyapatite should preferably be used as constituent materials for the ceramic composite of the present invention.

A slurry, in which primary particles of a bonding ceramic are dispersed, is interposed between the ceramic bodies as described above. In this case, when at least one of the ceramic bodies to be bonded is a porous ceramic body, the bonding ceramic in the slurry is embedded into the pores of the porous ceramic body. Thus, it becomes possible to increase the contacting surface area between one ceramic body and the other ceramic body. Further, it also becomes possible to bond the ceramic bodies such that an anchoring effect is obtained. As a result, the bonding strength between the ceramic bodies is enhanced.

When sintering the ceramic bodies between which the slurry has been interposed, the particles (primary particles) of the bonding ceramic in the slurry react with adjacent particles and then grow into larger particles. Repeating such particle growth allows the ceramic bodies to be bonded to each other.

In addition, since the strength of the sintered bonding ceramic is the same as that of the ceramic bodies, a ceramic composite having uniform strength can be obtained. Such a ceramic composite is capable of preventing the strength at the bonding area between one ceramic body and the other ceramic body from falling below that of other portions.

The disperse medium to be contained in the slurry should preferably be inorganic disperse medium such as water.

In this connection, it is to be noted that the slurry does not contain any water-soluble polymers such as binders which are commonly used as bonding materials. Thus, ceramic composites having no organic components can be obtained.

Accordingly, the ceramic composite of the present invention does not contain any organic components, thus eliminating the danger that these organic components will elute into the living body when this ceramic composite is used as a biocompatible material. This means that the ceramic composite of the present invention has excellent biosafety.

In addition, the aforementioned slurry does not contain any high-viscosity substances such as water-soluble polymers and the like, thus allowing the bonding ceramic to be dispersed in the slurry uniformly and easily. This means that the slurry used during the manufacture of the ceramic composite of the present invention has excellent workability and handling ability.

When a calcium phosphate-based ceramic is used as the bonding ceramic, the slurry in which primary particles of the bonding ceramic are dispersed may be prepared, for example, by a method (wet process) in which a phosphoric acid aqueous solution in the form of droplet is added to a calcium hydroxide slurry.

The bonding ceramic should preferably be constituted from the same ceramic material as that of at least one of the ceramic bodies to be bonded.

When the bonding ceramic in the slurry which is constituted from the same material as that of the ceramic bodies is used to bond the ceramic bodies together, it becomes possible to prevent boundary surface (interface) from being formed between the sintered ceramic bodies. Thus, the bonding strength of the ceramic composite can be enhanced or improved.

In this connection, the ceramic materials which is the same as those for the above-mentioned ceramic bodies may be used for a material for the bonding ceramics.

For the same reasons as those described with reference to the ceramic bodies, the ceramic material used for the bonding ceramic should be a calcium phosphate-based compound, preferably one with a Ca/P ratio of 1.0 to 2.0, and more preferably hydroxyapatite.

Although the content of the bonding ceramic in the slurry is not limited in any particular value, a content of about 0.1 to 20 vol % is preferred. When a content of the bonding ceramic is less than 0.1 vol %, there is a case that the bonding ceramic fails to exhibit an adequate effect, thereby resulting in inferior bonding strength. On the other hand, when a content of the bonding ceramic exceeds 20 vol %, the fluidity of the slurry becomes lowered, which may result in poor handling ability and workability.

The particles (primary particles) of the bonding ceramic should have an average grain size of 0.05 to 0.5 $\mu$m, and preferably 0.1 to 0.3 $\mu$m.

When the average grain size of the bonding ceramic is less than 0.05 µm, there is a case that an adequate bonding effect will not be obtained. On the other hand, when the average grain size exceeds 0.5 µm, it is not always possible to keep uniform density of the bonding ceramic in the slurry. Consequently, there is a case that nonuniform sintering and dispersion in the bonding strength will occur.

No limitations are imposed on the method for applying the above-mentioned slurry to the bonding surface. Examples of the applying methods include a method in which the slurry is merely applied to the bonding surface, a method in which the slurry is impregnated into the bonding surface, a method in which the slurry is sprayed against the bonding surface, and a method in which the slurry is dropped onto the bonding surface. Further, it is also possible to use a method in which the bonding surfaces of the ceramic bodies are immersed in the slurry. Furthermore, the slurry may also be applied to the bonding surface by a combination of these methods.

After the slurry has been applied between the ceramic bodies, the two ceramic bodies may be compressed to evenly spread the slurry across the bonding surfaces thereof, if necessary.

Examples of sintering techniques used in the method for manufacturing a ceramic composite according to the present invention include non-pressure sintering methods such as normal pressure sintering, hot plasma sintering, microwave sintering and the like; and pressure sintering methods such as hot pressing (HP), spark plasma sintering (SPS), hot isostatic pressing (HIP) and the like. Among these methods, the non-pressure sintering methods should preferably be utilized to manufacture the ceramic composite of the present invention.

The above-described pressure sintering methods make it possible to manufacture ceramic composites having complex shapes.

In contrast with the pressure sintering methods, the non-pressure sintering methods make sintering equipment and sintering process more simple, and also make it possible to improve manufacturing efficiency.

The sintering temperature is appropriately set in accordance with the sintering methods or materials constituting the ceramic bodies. This temperature is preferably 900 to 1300° C., and more preferably 1000 to 1200° C. When the sintering temperature is lower than 900° C., it is sometimes impossible to obtain adequate bonding strength due to inferior sintering. On the other hand, when the temperature exceeds 1300° C., there is a case that heat will induce decomposition in the bonding ceramic and the ceramic materials constituting the ceramic bodies.

The sintering time is not subject to any particular limitations. When sintering the ceramic bodies at the above-described sintering temperatures, the sintering time is preferably 0.1 to 6 hours, and more preferably 0.5 to 4 hours.

Although, in the above explanation, ceramic bodies which have already been sintered are used, it is also possible to use unsintered ceramic bodies (unsintered compacts) to form the ceramic composite of the present invention.

Further, in order to manufacture the ceramic composite of the present invention, it is also possible to interpose the slurry as described above between a sintered compact and an unsintered compact, and then sinter them.

According to the above-described method of the present invention, the manufactured ceramic composite is completely integrated. In addition, no boundary surface (interface) is formed between the bonded (sintered) ceramic bodies after sintering. Consequently, the method of the present invention makes it possible to manufacture a ceramic composite whose strength is substantially uniform throughout.

In addition, the absence of a boundary surface in such a ceramic composite makes it possible to prevent the strength of the bonding area between the ceramic bodies from being adversely affected after sintering. Further, the absence of such a boundary surface also makes it possible to prevent one ceramic body from peeling off from the other ceramic body after sintering. Furthermore, the method of the present invention also makes it possible to prevent cracks or the like from developing in the bonding area between the ceramic bodies after sintering.

In addition, when hydroxyapatite or another biocompatible material is used as a constituent material for the bonding ceramic and the ceramic bodies, it becomes possible to manufacture a ceramic composite suitable for artificial dental implants, bone replacement materials such as vertebral spacers and the like.

In this regard, it is to be noted that in this invention a slurry, in which primary particles of a ceramic are dispersed, is used to manufacture the ceramic composite and the slurry does not contain any bonding materials such as resins and the like. Therefore, it is possible to prevent the manufactured ceramic composite from containing any resin components or the like.

As described above, the ceramic composite of the present invention does not contain any resin components or the like, thus eliminating the danger that these resin components or the like will elute into the living body even when this ceramic composite is used as a biocompatible material. This means that the ceramic composite of the present invention has excellent biosafety.

In addition, according to the method for manufacturing a ceramic composite of the present invention, it is possible to bond ceramic bodies having different porosities together. This makes it possible to manufacture a ceramic composite in which different sections exhibit different functions despite the fact that the composite is a monolithic structure.

In the above, the method for manufacturing a ceramic composite in accordance with the present invention, and a ceramic composite manufactured by this method were described. In this connection, however, it should be noted that the present invention is not limited to the embodiments described above. For example, the ceramic bodies described above may contain any metal materials (for example, titanium) which are harmless to the living body, besides the ceramic materials. In addition, three or more ceramic bodies may be bonded together.

EXAMPLES

Hereinafter, specific examples of the present invention will be described.

1. Manufacture of Ceramic Composite

Example 1

A phosphoric acid aqueous solution in the form of droplet was added to a calcium hydroxide slurry to obtain a hydroxyapatite slurry containing 10 vol % primary particles of a hydroxyapatite having a Ca/P ratio of 1.67 and an average grain size of 0.1 µm.

Further, the hydroxyapatite slurry obtained in accordance with the above-described wet process was sprayed and then dried to obtain the spherical powder (secondary particles) of hydroxyapatite. Then, after pre-sintering the obtained spherical powder at 700° C., it was pulverized.

Subsequently, the pulverized hydroxyapatite powder was added in a predetermined ratio to an aqueous solution of natural macromolecular compound such as methylcellulose and the like. Then, the mixed solution was agitated until the solution was frothed (foamed). The foamed solution was subsequently dried at about 80° C. to obtain unsintered ceramic bodies 3 and 5 as shown in FIG. 1.

In this regard, it should be noted that the degree of formation of foam in the mixed solution for the ceramic body 3 was different from that in the mixed solution for the ceramic body 5. With this result, the obtained ceramic bodies 3 and 5 had different porosities.

Figure 2:
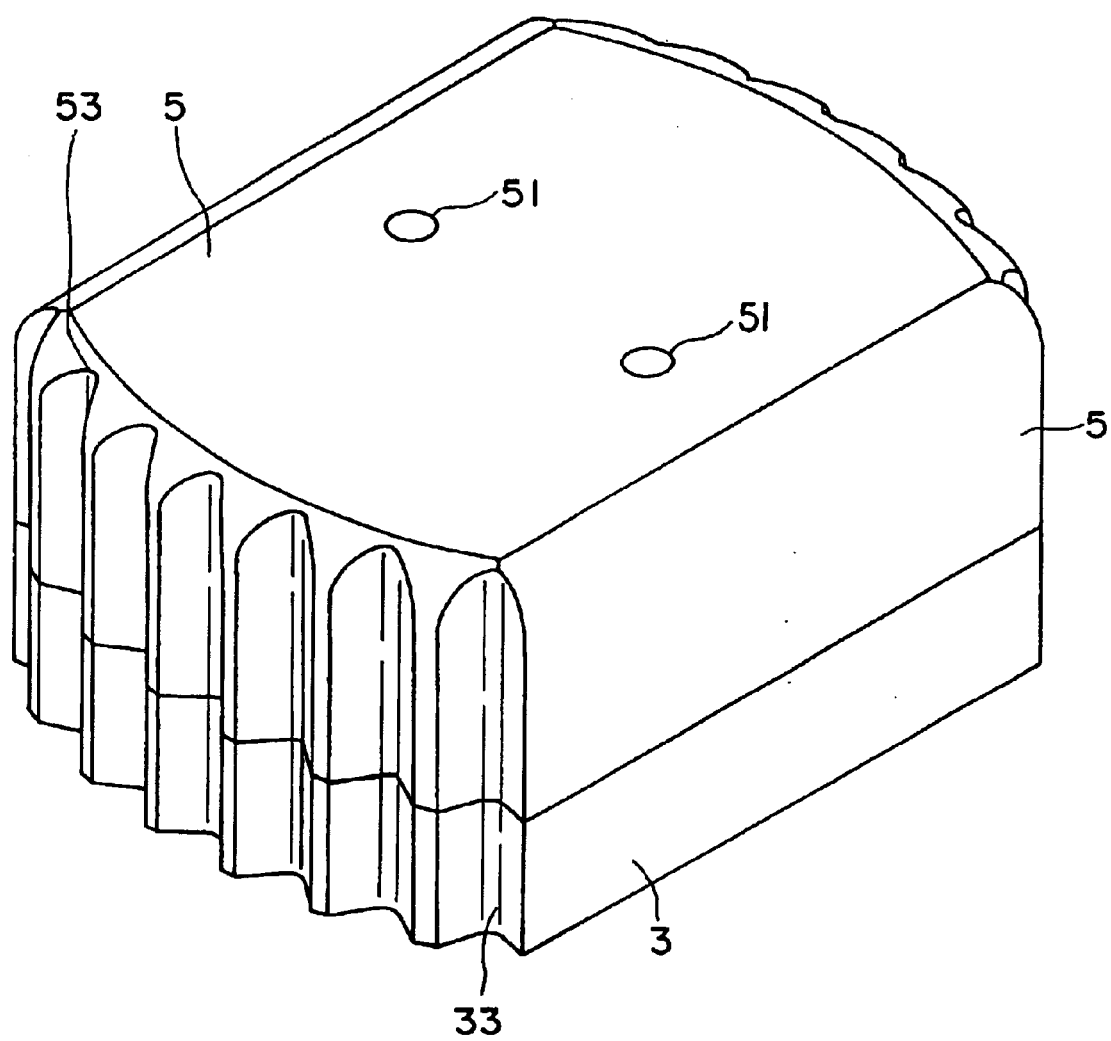
FIG. 2 is a perspective view which shows a state that the ceramic bodies in FIG. 1 are superposed.
Figure 3:
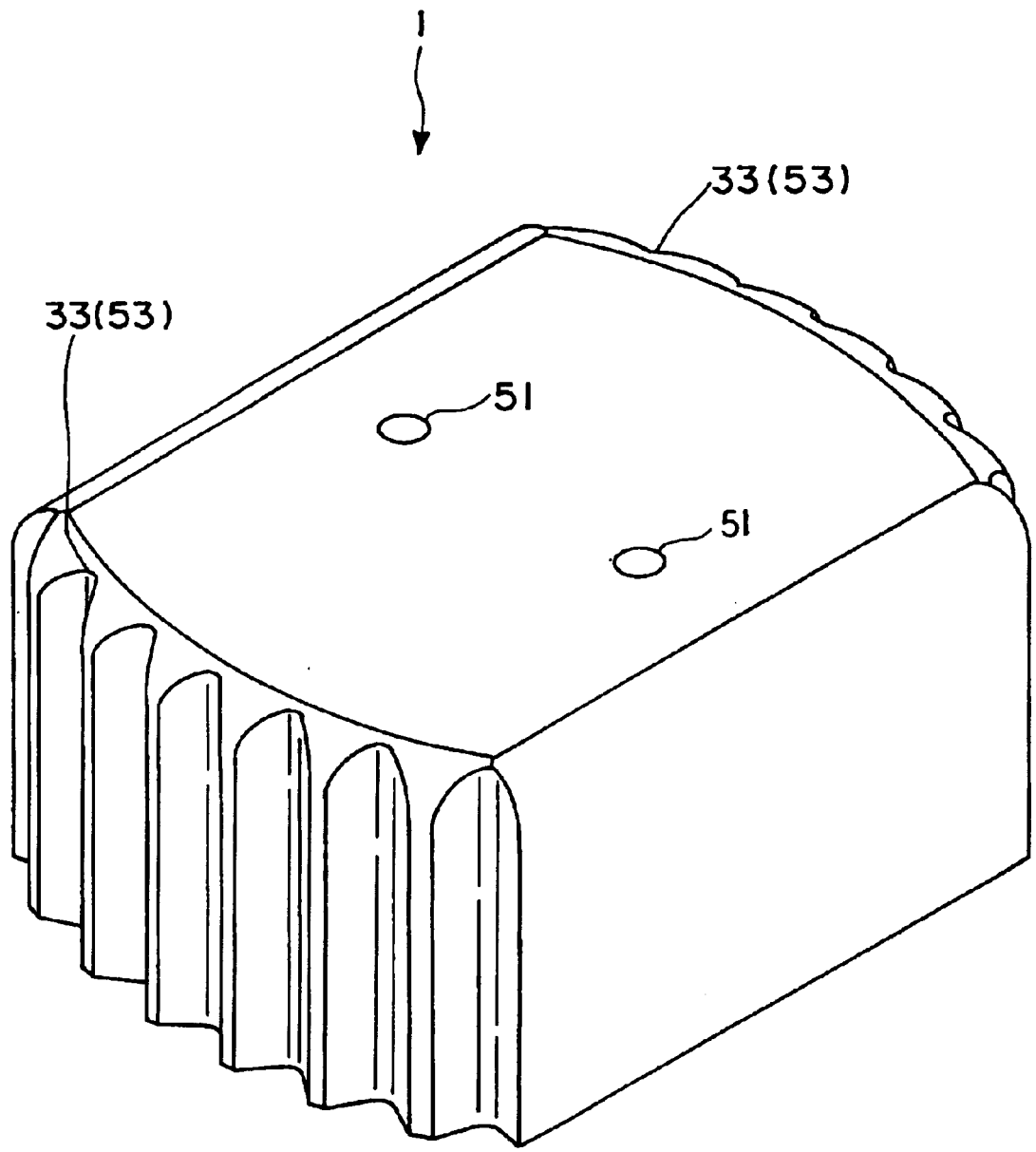
FIG. 3 is a perspective view which shows a ceramic composite manufactured in accordance with the method of the present invention.

As shown in FIGS. 1 to 3, two openings 51 were provided near the center of the top surface of the ceramic body 5. The presence of these openings made it possible to ascertain that the ceramic body 5 had a higher porosity than the ceramic body 3.

Subsequently, a slurry 4, which had been prepared in advance, was applied in an appropriate amount to the bonding surface 35 of the ceramic body 3 as shown in FIG. 1, and then the ceramic body 5 was superposed thereon (see FIG. 2).

Then, the ceramic bodies 3 and 5 in the state shown in FIG. 2 were sintered for 2 hours at a sintering temperature of 1200° C. by a normal-pressure sintering method to obtain a ceramic composite for a vertebral spacer 1.

In the state that the sintering process had been completed, a portion of the ceramic composite (vertebral spacer) 1 formed from the ceramic body 3 had a porosity of 30%, and a portion of the ceramic composite (vertebral spacer) 1 that formed from the ceramic body 5 had a porosity of 55%.

The obtained vertebral spacer 1 had a shape of generally rectangular parallelepiped (width: 15 mm, maximum length: 20 mm, height: 7 mm). Further, as shown in FIG. 3, engagement grooves 33 (53) were formed in the facing lateral surfaces of the vertebral spacer 1. These engagement grooves 33 (53) were formed to allow the vertebral spacer 1 to be securely fixed in place in an implantation area. In other words, the engagement grooves 33 (53) prevent the vertebral spacer 1 from being dislodged from the implantation area.

Example 2

A ceramic body 3 whose porosity after sintering was 40%, and a ceramic body 5 whose porosity after sintering was 50% were used to manufacture a vertebral spacer 1. In this regard, the vertebral spacer 1 was manufactured in the same manner as in Example 1 except that the porosities of the ceramic bodies were changed as described above.

2. Evaluation of the Manufactured Ceramic Composites

The vertebral spacers 1 manufactured in Examples 1 and 2 were evaluated. To perform this evaluation, the condition of the bonding area (boundary surfaces) between the sintered ceramic bodies 3 and 5 was observed visually and under an electron microscope.

In this connection, to observe the vertebral spacers 1 under an electron microscope, the vertebral spacers 1 were cut along a plane perpendicular to the bonding area (bonding surfaces) between the ceramic bodies 3 and 5. An evaluation was conducted by observing these cross sections under an electron microscope.

Evaluation results in the case where the vertebral spacers 1 were evaluated visually were as follows.

The ceramic bodies 3 and 5 of the vertebral spacers 1 manufactured according to Examples 1 and 2 were monolithically (completely) integrated as shown in FIG. 3. For this reason, it was impossible to visually check the condition of the boundary surface between the ceramic bodies 3 and 5.

Next, evaluation results in the case where the vertebral spacers 1 were evaluated under the electron microscope were as follows.

Figure 4:
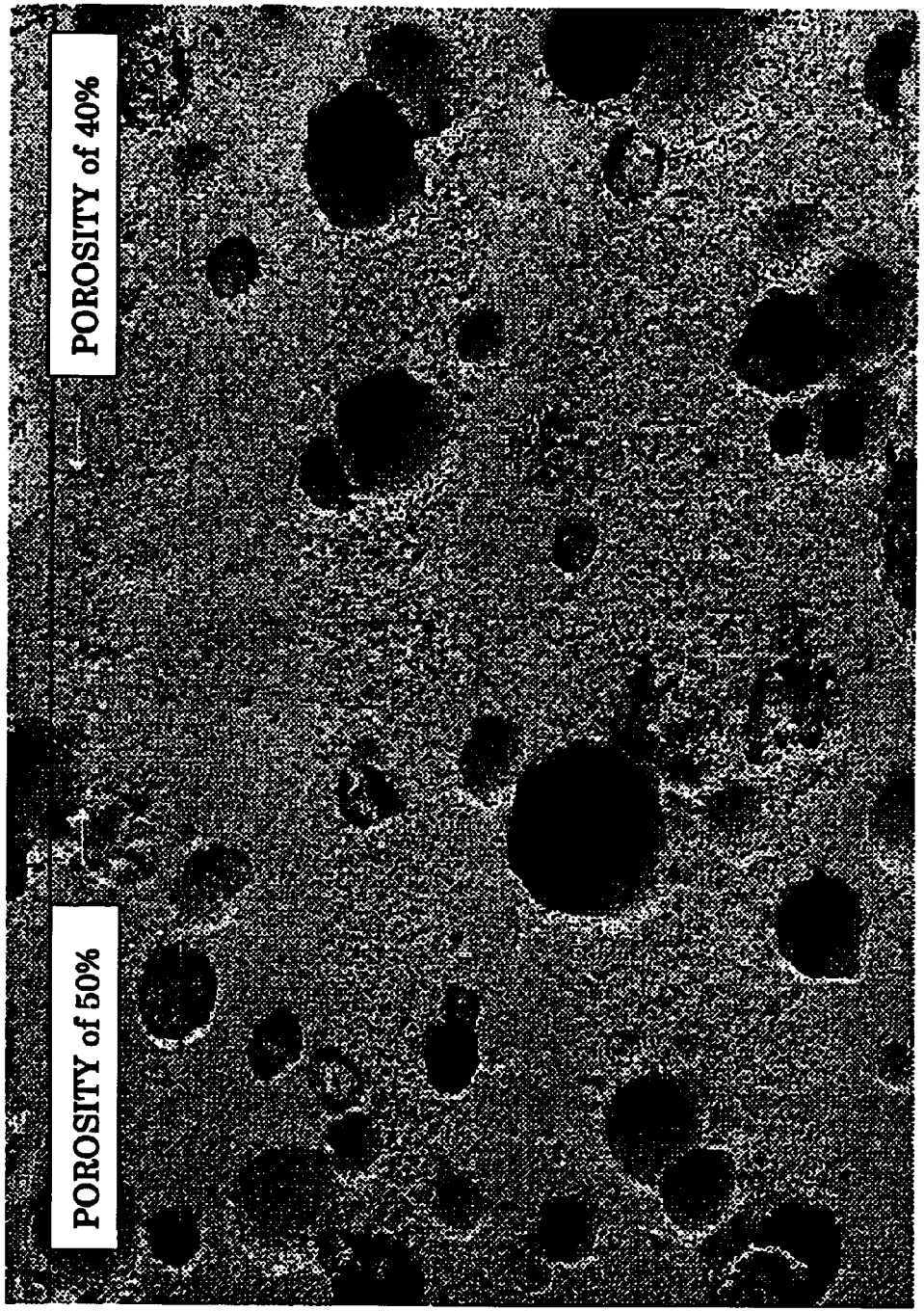
FIG. 4 is an electron photomicrograph (magnification: ×40) which shows a cross section of the ceramic composite manufactured in accordance with the method of the present invention.

FIG. 4 is an electron photomicrograph (magnification: ×40) which shows the vertebral spacer 1 manufactured in Example 2. This electron photomicrograph shows a plane (cross section) perpendicular to the bonding area (boundary surface) between the sintered ceramic bodies 3 and 5. In addition, the right half of the electron photomicrograph shows the portion of the sintered vertebral spacer 1 that corresponds to the ceramic body 3 (porosity: 40%), and the left half of the electron photomicrograph shows the portion of the vertebral spacer 1 that corresponds to the ceramic body 5 (porosity: 50%).

The photomicrograph in FIG. 4 shows that no boundary surface (interface) has been formed between the sintered ceramic bodies 3 and 5. In other words, it has been found that the boundary surface existing between the ceramic bodies 3 and 5 prior to sintering has been eliminated during the sintering process.

It has been also found that a heterogeneous layer which is distinguished from the portions derived from the ceramic bodies 3 and 5 was absent in the area between the sintered ceramic bodies.

In the same manner as in the above, the vertebral spacer manufactured in Example 1 was evaluated using the electron microscope. Observation result of the vertebral spacer 1 manufactured in Example 1 was the same as that of the vertebral spacer 1 manufactured in Example 2.

3. Application of Vertebral Spacer (Ceramic Composite) into Living Body

Hereinafter, an evaluation for the case where the vertebral spacer (ceramic composite) was applied into a living body will be described with reference to FIGS. 5 and 6.

Figure 5:
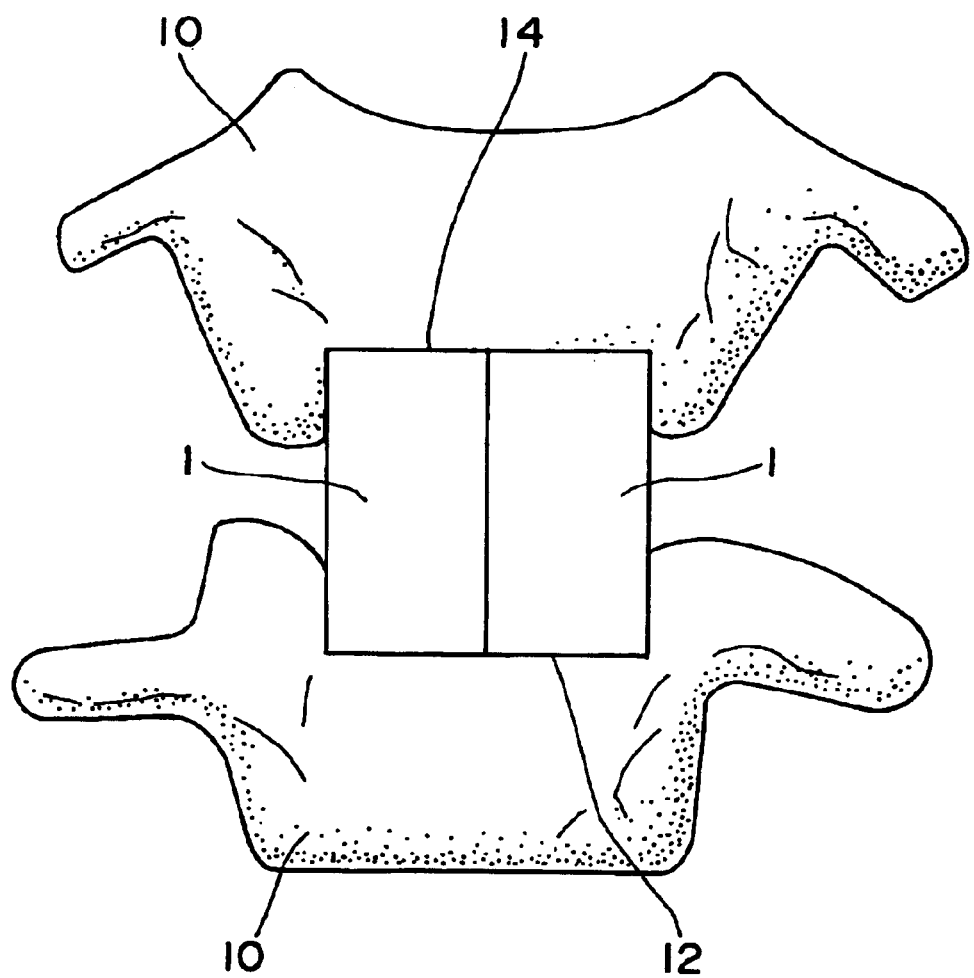
FIG. 5 is a front view which shows a state in which a vertebral spacer formed from the ceramic composite of the present invention is implanted into and fixed to a cervical vertebrae.
Figure 6:
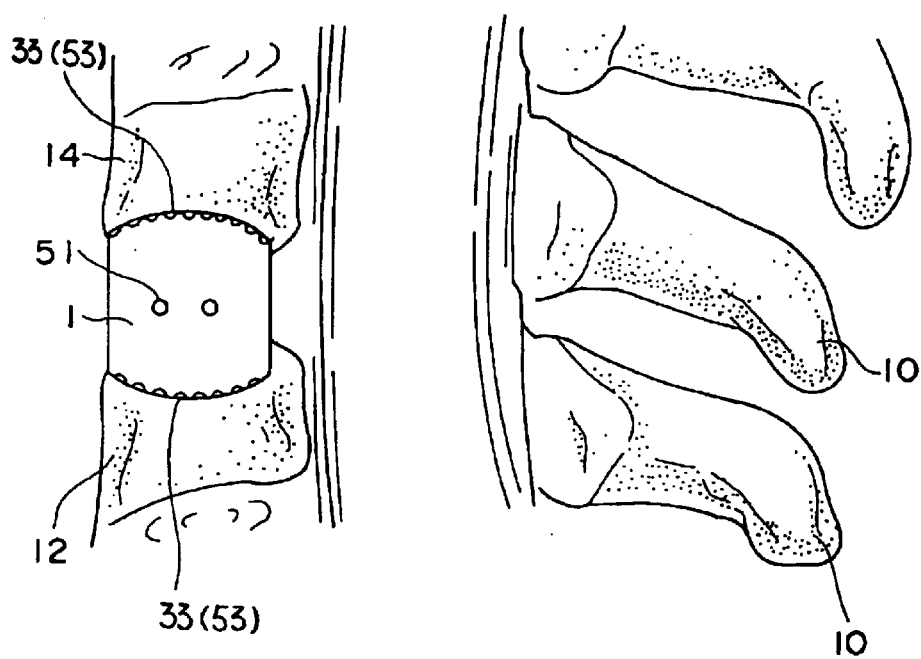
FIG. 6 is a side view which shows a state in which the vertebral spacer is implanted into and fixed to a cervical vertebrae.

FIG. 5 is a front view which shows a state in which the vertebral spacer 1 is implanted into and fixed to cervical vertebrae 10, and FIG. 6 is a side view thereof.

First, two vertebral spacers 1 were prepared in the same manner as in Example 1, and further two vertebral spacers 1 were prepared in the same manner as in Example 2.

Next, an operator (or a surgeon) executed the operation of decompressing and fusing anterior cervical vertebrae to a patient who needs the decompression and fusion of his (or her) anterior cervical vertebrae across the space between vertebral bodies, by cutting and eliminating the region of the vertebral bodies corresponding to the compressed area of the spinal cord, thereby decompressing for the cervical vertebrae 10 was performed.

After the cervical vertebrae 10 had been decompressed, two superposed vertebral spacers 1 (prepared in advance) were inserted (implanted) into the space between the vertebral bodies 12 and 14 of the cervical vertebrae 10, as shown in FIGS. 5 and 6. During the insertion of the vertebral spacers 1 into the cervical vertebrae 10, an engagement was made between the engagement grooves and the vertebral bodies 12 and 14 to fix firmly the two superposed vertebral spacers 1 in the space.

With respect to the state shown in FIG. 5, it should be noted that the two vertebral spacers 1 were superposed and inserted such that the low-porosity portions are positioned on the inside thereof (that is, the low-porosity portions face to each other), and the high-porosity portions are positioned on the outside.

In this way, it was possible to expand the constricted portions of the cervical vertebrae and to maintain this expanded state.

Further, X-ray imaging observation was carried out immediately after surgery, and the obtained image showed transparent layers indicating the presence of spaces in the interface portions between the vertebral spacers 1 and the vertebral bodies 12 and 14. However, these transparent layers have disappeared in a relatively short time after surgery as a result of bone cohesion.

Furthermore, since the strength of the vertebral spacers 1 on the whole was ensured by the low-porosity portions positioned inside thereof, it was possible to keep the distance between the vertebral bodies 12 and 14 in a desired interval.

As described above, the method of manufacturing the ceramic composite according to the present invention makes it possible to bond a plurality of ceramic bodies with a simple technique.

In addition, according to the present invention, the slurry in which primary particles of a bonding ceramic are dispersed is applied to the bonding surface of one of the ceramic bodies to be bonded, and sintering such ceramic bodies makes it possible to obtain the ceramic composite having an excellent bonding strength. Further, it becomes possible to completely integrate the ceramic bodies with each other, thereby preventing the strength at the bonding area between the sintered ceramic bodies from being deteriorated.

Further, according to the present invention, it is possible to easily manufacture ceramic composites having complex shapes and to bond ceramic bodies having different porosities. Bonding ceramic bodies having different porosities together makes it possible to obtain a ceramic composite in which different sections exhibit different functions. Therefore, it becomes possible to manufacture, with a simple technique, a ceramic composite (e.g., biocompatible materials such as artificial dental implants, bone replacement materials, dental cements and the like) having the required strength and excellent bioaffinity and biosafety.

Furthermore, according to the present invention, the slurry that is applied to the ceramic bodies to be bonded does not contain any water-soluble polymers such as binders. This means that ceramic composites that do not contain any organic components can be manufactured. Accordingly, the ceramic composite of the present invention eliminates the danger that these organic components will elute into the living body when this ceramic composite is used as a biocompatible material.

Finally, it is to be understood that many changes and additions may be made to the embodiments described above without departing from the scope and spirit of the invention as defined in the appended Claims.

Further, it is also to be understood that the present disclosure relates to subject matter contained in Japanese Patent Application No. 10-340459 (filed on Nov. 30, 1998) which is expressly incorporated herein by reference in its entirely.

What is claimed is:

1. A method of manufacturing a ceramic composite, the method comprising:
preparing at least two porous ceramic bodies to be bonded together, each of the at least two porous ceramic bodies having a bonding surface and a porosity of 15 to 70%, each of the at least two ceramic bodies being formed of a calcium phosphate-based compound, and the at least two porous ceramic bodies having a different porosity from each other;
preparing a slurry in which primary particles of a bonding ceramic are dispersed, the bonding ceramic being formed of the same material as that of each ceramic body, said slurry being synthesized by merely adding a phosphoric compound to a calcium compound slurry;
applying the slurry to the bonding surface of at least one of the ceramic bodies to be bonded; and
sintering the ceramic bodies between which the slurry has been interposed to obtain fusing and growing of the primary particles of a bonding ceramic in the slurry during the sintering and bonding of the at least two ceramic bodies together so as to provide an anchoring effect between the ceramic bodies due to a combination of the porous ceramic bodies and the bonding ceramic.

2. The method of manufacturing the ceramic composite as claimed in claim 1, wherein the at least two ceramics bodies have the identical compositions.

3. The method of manufacturing the ceramic composite as claimed in claim 1, wherein at least one of the ceramic bodies is composed of calcium phosphate-based compounds with a Ca/P ratio of 1.0 to 2.0.

4. The method of manufacturing the ceramic composite as claimed in claim 2, wherein the calcium phosphate-based compounds include hydroxyapatite.

5. The method of manufacturing the ceramic composite as claimed in claim 1, wherein the content of the bonding ceramic in the slurry is 0.1 to 20 vol %.

6. The method of manufacturing the ceramic composite as claimed in claim 1, wherein the particles of the bonding ceramic have an average grain size of 0.05 to 0.5 $\mu$m.

7. The method of manufacturing the ceramic composite as claimed in claim 1, wherein the bonding ceramic is composed of calcium phosphate-based compounds with a Ca/P ratio of 1.0 to 2.0.

8. The method of manufacturing the ceramic composite as claimed in claim 1, wherein the calcium phosphate-based compounds include hydroxyapatite.

9. The method of manufacturing the ceramic composite as claimed in claim 1, wherein the step of sintering the ceramic bodies is carried out in accordance with a non-pressure sintering method.

10. The method of manufacturing the ceramic composite as claimed in claim 1, wherein the step of sintering the ceramic bodies is carried out at a temperature from 900 to 1300° C.

11. The method of manufacturing the ceramic composite as claimed in claim 1, wherein the slurry does not contain any resin components therein.

12. A ceramic composite manufactured in accordance with the method as claimed in claim 1.

13. A bone replacement material manufactured in accordance with the method as claimed in claim 1.

14. A method of manufacturing a ceramic composite for a biocompatible material, the method comprising:
preparing at least two porous ceramic bodies to be bonded together, each of the at least two porous ceramic bodies having a bonding surface and a porosity of 15 to 70%, and the at least two porous ceramic bodies having a different porosity from each other;
preparing a slurry in which primary particles of a bonding ceramic are dispersed, said slurry containing no organic components therein for preventing elution of organic components into a human body;
applying the slurry to the bonding surface of the at least one of the ceramic bodies to be bonded; and
sintering the ceramic bodies between which the slurry has been interposed to obtain fusing and growing of the primary particles of a bonding ceramic in the slurry during the sintering and bonding of the at least two ceramic bodies together so as to provide an anchoring effect between the ceramic bodies due to a combination of the porous ceramic bodies and the bonding ceramic.

15. The method of manufacturing the ceramic composite as claimed in claim 14, wherein the bonding ceramic is formed of the same material as that of each ceramic body.

* * * * *